US009440379B2

(12) United States Patent
Smith et al.

(10) Patent No.: US 9,440,379 B2
(45) Date of Patent: Sep. 13, 2016

(54) DEVICE FOR COATING INTRAMEDULLARY RODS WITH CEMENT (71) Applicant: Biomet Manufacturing, LLC, Warsaw, IN (US)

(72) Inventors: Daniel B. Smith, Warsaw, IN (US); Katie M. Schindler, Fort Wayne, IN (US); Grant D. Cunningham, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/691,070

(22) Filed: Apr. 20, 2015

(65) Prior Publication Data

US 2015/0321389 A1 Nov. 12, 2015

Related U.S. Application Data (62) Division of application No. 13/547,331, filed on Jul. 12, 2012, now Pat. No. 9,017,055.

(51) Int. Cl.
*B29C 39/10* (2006.01)
*B29C 39/24* (2006.01)
*A61B 17/72* (2006.01)
*B29C 39/26* (2006.01)
(Continued)

(52) U.S. Cl.
CPC ............... *B29C 39/10* (2013.01); *A61B 17/72* (2013.01); *B29C 39/24* (2013.01); *B29C 39/26* (2013.01); *A61B 2017/00526* (2013.01); *A61B 2017/00889* (2013.01); *B29C 2033/0005* (2013.01); *B29K 2705/00* (2013.01); *B29L 2031/7546* (2013.01)

(58) Field of Classification Search
CPC ....... B29C 39/10; B29C 39/24; A61B 17/72; B61B 2017/00526; B29K 2705/00; B29L 2031/7546
See application file for complete search history.

(56) References Cited

U.S. PATENT DOCUMENTS 5,098,434 A 3/1992 Serbousek
5,133,771 A 7/1992 Duncan et al.
(Continued)

FOREIGN PATENT DOCUMENTS

CN 101754723 A 6/2010
CN 101801286 A 8/2010
(Continued)

OTHER PUBLICATIONS

Conway, Janet, M.D., "How to Create Antibiotic Cement-Coated Intramedullary Nails Using the Exterminator System", International Center for Limb Lengthening, Apr. 30, 2010, <http://www.youtube.com/watch?v=b_YF6pwb9l>.
(Continued)

*Primary Examiner* — Robert B Davis
(74) *Attorney, Agent, or Firm* — Schwegman Lundberg & Woessner, P.A.

(57) ABSTRACT

A mold for forming a coated intramedullary (IM) nail can include a tubular member having an insertion end and an opposite end. The tubular member can comprise a sidewall extending along a longitudinal axis between an outer surface and an inner surface. The sidewall can define at least one threaded inlet port therealong. The tubular member can be configured to receive the IM nail therein. The tubular member can be further configured to locate a flowable material against the IM nail within the inner surface.

12 Claims, 9 Drawing Sheets (51) Int. Cl.
  *B29K 705/00* (2006.01)
  *B29L 31/00* (2006.01)
  *A61B 17/00* (2006.01)
  *B29C 33/00* (2006.01)

(56) References Cited

U.S. PATENT DOCUMENTS

| | | |
|---|---|---|
| 5,360,448 A | 11/1994 | Thramann |
| 5,433,718 A | 7/1995 | Brinker |
| 5,489,306 A | 2/1996 | Gorski |
| 5,618,286 A | 4/1997 | Brinker |
| 5,868,747 A | 2/1999 | Ochoa et al. |
| 6,183,255 B1 | 2/2001 | Oshida |
| 6,554,867 B1 | 4/2003 | Joos |
| 6,911,249 B2 | 6/2005 | Wagner et al. |
| 7,637,729 B2 | 12/2009 | Hartman et al. |
| 9,017,055 B2 | 4/2015 | Smith et al. |
| 2002/0038149 A1 | 3/2002 | Hall et al. |
| 2008/0262630 A1 | 10/2008 | Fulmer et al. |
| 2009/0043307 A1 | 2/2009 | Faccioli et al. |
| 2011/0208189 A1 | 8/2011 | Faccioli et al. |
| 2012/0089148 A1 | 4/2012 | Vaidya |

FOREIGN PATENT DOCUMENTS

| | | |
|---|---|---|
| EP | 2872309 A1 | 5/2015 |
| WO | 2010/088531 A2 | 8/2010 |
| WO | WO2014011843 A1 | 1/2014 |

OTHER PUBLICATIONS

"U.S. Appl. No. 13/547,331, Notice of Allowance mailed Dec. 31, 2014", 5 pgs.

Chinese Application Serial No. 2013800368182, Office Action mailed Mar. 29, 2016, 14 pgs.

European Application Serial No. 13739915.0, Communication Pursuant to Article 94(3) EPC mailed Dec. 22, 2015, 3 pgs.

European Application Serial No. 13739915.0, Office Action mailed Mar. 24, 2015, 2 pgs.

European Application Serial No. 13739915.0, Response filed Sep. 2, 2015 to Office Action mailed Mar. 24, 2015, 13 pgs.

DEVICE FOR COATING INTRAMEDULLARY RODS WITH CEMENT

CROSS-REFERENCE TO RELATED APPLICATION

This application is a divisional of U.S. application Ser. No. 13/547,331, filed on Jul. 12, 2012. The entire disclosure of which is incorporated herein by reference.

INTRODUCTION

The present technology relates generally to cement coated rods and more specifically to a mold and related method for coating intramedullary (IM) rods with an antibiotic-loaded hardenable material.

In some instances during treatment of fractures on various long bones, such as diaphyseal fractures of the femur, tibia, and humerus bones, it may be desirable to introduce a longitudinal rod or nail through the IM canal of the bone to assist in stabilizing long bones during bone healing. In these instances, it also may be desirable to provide an IM nail that is coated with antibiotic-loaded cement to assist in treatment or prevention of infection. The IM nail can have an elongated metallic member that includes one or more cylindrical cavities that can be perpendicular to the long axis of the IM nail for receiving a fastener element, such as a transcortical screw. The IM nail can be positioned within the medullary cavity and can be secured to the proximal and distal fracture segments using transcortical screws, which penetrate both cortices of the bone, as well as pass through the cylindrical cavities formed in the IM nail.

In some cases, it can be challenging to produce an IM nail having an antibiotic-loaded cement coating. In some known examples, antibiotic-loaded cement can be introduced into an open end of a tube and an IM nail can be subsequently introduced into the tube. Once the antibiotic-loaded cement cures, the tube can be removed. This configuration and method can be unfavorable to a user as the flowable cement can be quite viscous. In this regard, filling a relatively long tube with such material can be difficult. In examples where the tube is formed of a relatively thin-walled elastomeric material, filling the tube can become more difficult as the tubing may expand during the introduction of the cement. In this regard, cement may be inhibited from flowing down the length of the tube. In other examples, the tubing may expand during the delivery stroke, and then contract, allowing cement to flow back into the cement delivery device between delivery strokes. In examples where the flowable material is introduced into the tube before insertion of the IM rod, the insertion of the IM rod can be uncontrolled and generally messy as the cement out of the tube and/or can easily flow onto parts of the IM rod where it is undesired.

SUMMARY

This section provides a general summary of the disclosure, and is not a comprehensive disclosure of its full scope or all of its features.

A mold for forming a coated intramedullary (IM) nail can include a tubular member having an insertion end and an opposite end. The tubular member can comprise a sidewall extending along a longitudinal axis between an outer surface and an inner surface. The sidewall can define at least one threaded inlet port therealong. The tubular member can be configured to receive the IM nail therein. The tubular member can be further configured to locate a flowable material against the IM nail and the inner surface of the tubular member.

According to additional features, the inner surface of the tubular member can comprise at least one inwardly and radially extending protrusion. In other features, the inner surface can comprise three inwardly extending protrusions radially spaced substantially equally to each other on the inner surface. The protrusions can extend substantially along the length of the tubular member between the insertion end and an opposite end.

According to other features, the protrusions can each include longitudinally spaced nibs extending inwardly toward the longitudinal axis. Each nib can have a nail engaging surface configured to engage the nail and offset the nail inwardly along the longitudinal axis and spaced from a remainder of the protrusion. The opposite end of the tubular member can be closed and define a concave surface. The tubular member can further comprise a first inlet port formed through the sidewall and configured to accept the flowable material therethrough. The first inlet port can comprise a threaded port extending outwardly from the outer surface.

According to still other features, the tubular member can further comprise a plurality of threaded inlet ports spaced from each other and formed through the sidewall configured to accept flowable material therethrough. The sidewall can comprise a plurality of vent holes therealong. The plurality of vent holes can comprise at least one distinct row of vent holes formed longitudinally along the sidewall. According to one configuration, the plurality of vent holes can comprise at least two distinct rows of vent holes, each row radially spaced between two adjacent protrusions. According to one configuration, the mold can be transparent. In one example, the mold can be flexible. In one configuration, the mold can be cuttable. The mold can be formed of a material that releases from cured flowable material. The material can comprise silicone. In some examples, the silicone can be reinforced silicone. In one configuration, the mold can further comprise a pull member disposed on the tubular member. The pull member can be configured to influence formation of a slit or cut on the tubular member upon pulling for removing the tubular member subsequent to curing of the flowable material. A sheath can be configured to be disposed onto the IM nail and inhibit introduction of the flowable material into the IM nail.

A method of coating an intramedullary (IM) nail with flowable material can include, advancing the IM nail into a tubular member from an insertion end of the tubular member toward an opposite end of the tubular member. The flowable material can be advanced through a first port defined through a sidewall at a first location on the tubular member. Subsequent to curing of the flowable material, the tubular member can be removed from the IM nail having the cured flowable material thereon.

The method can further comprise advancing the flowable material through a second port through the sidewall at a second location, distinct from the first location, on the tubular member. According to other features, the method can further comprise observing the flowable material advancing within the tubular member. The advancing of the flowable material can be stopped through the first port based on the flowable material advancing substantially toward the second port.

According to other features, the method can further comprise slidably translating the IM nail along at least two longitudinally extending protrusions formed on the inner cylindrical surface of the sidewall. The method can further comprise coupling a flowable material delivery device to a boss formed on the tubular member proximate to the first port. In one example, coupling can include one of threadably coupling, luer lock coupling, and nozzle coupling the flowable material delivery device to the tubular member. According to additional features, advancing the IM nail can comprise advancing the IM nail into the tubular member until a distal end of the IM nail engages a concave surface at the opposite end of the tubular member. Removing the tubular member can comprise cutting the tubular member away from the coated IM nail. Removing the tubular member can comprise pulling a pull member disposed on the tubular member causing a slit to the formed along the tubular member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

The following description of technology is merely exemplary in nature of the subject matter, manufacture and use of one or more disclosures, and is not intended to limit the scope, application, or uses of any specific disclosure claimed in this application or in such other applications as may be filed claiming priority to this application, or patents issuing therefrom. Moreover, although the following description and illustrations refer specifically to a mold and related method for coating an IM nail, it will be understood that the molds and related methods disclosed herein may be applied to other implants. In addition, it will be understood that the terms "nail" and "rod" are used herein interchangeably to refer to the same or similar components. Furthermore, while the molds and related methods disclosed herein are specifically directed toward fabrication of antibiotic-loaded, cement-coated rods, the molds and methods disclosed herein may also be adapted to introduce other flowable material onto a surface of a prosthetic implant. Moreover, the molds and related methods disclosed herein may be used to create antibiotic-loaded, cement-coated implants applicable for use with other bones in the body. Therefore, it will be understood that the present description and the claims are applicable to any appropriate bone in the body. A non-limiting discussion of terms and phrases intended to aid understanding of the present technology is provided at the end of this Detailed Description.

Figure 1:
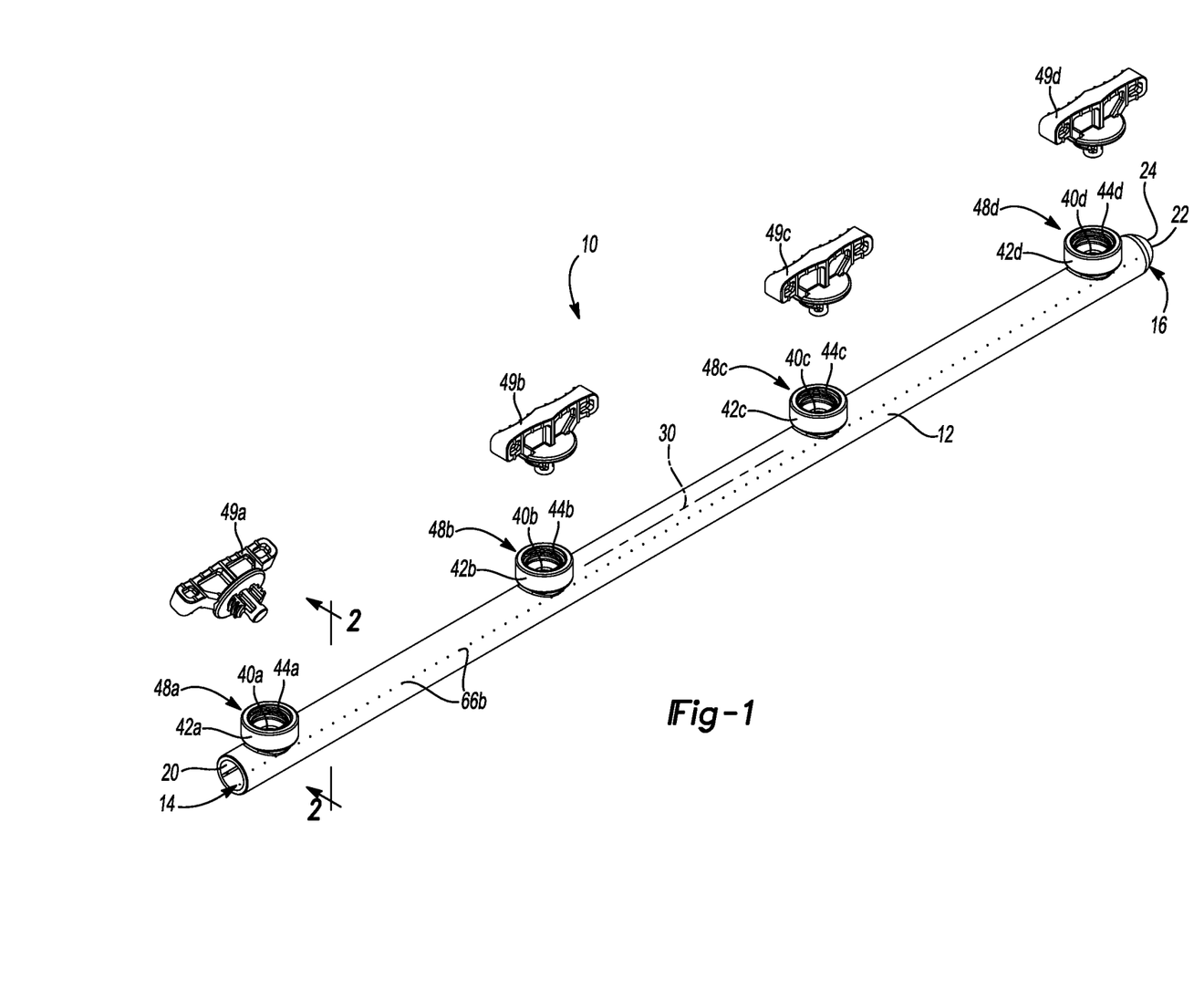
FIG. 1 is a side perspective view of a mold for forming a coated IM nail constructed in accordance to one example of the present teachings.

With initial reference to FIG. 1, a mold that may be used to form a coated intramedullary (IM) nail according to one example of the present disclosure is shown and generally identified at reference numeral 10. The mold 10 can include a tubular member 12 having an insertion end 14 and an opposite end 16. In the example shown, the insertion end 14 defines an opening whereas the opposite end 16 provides a closed end 22. In the example shown, the closed end 22 can have a generally convex outer surface 24. The tubular member 12 can extend generally along a longitudinal axis 30.

Figure 2:
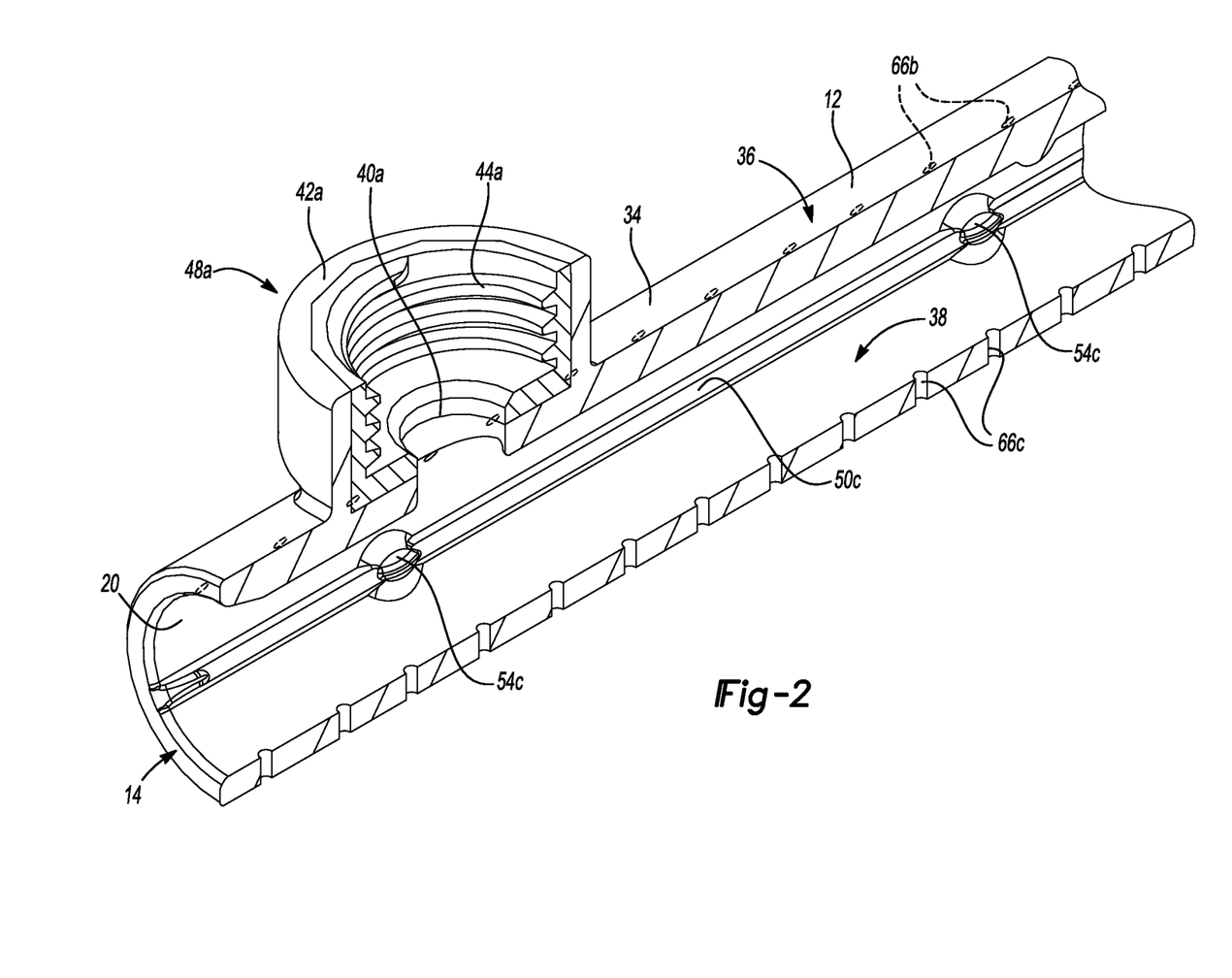
FIG. 2 is a partial cross-sectional view of the mold taken along lines 2-2 of FIG. 1.

With continued reference to FIG. 1 and additional reference now to FIG. 2, the tubular member 12 can have a sidewall 34 that has an outer surface 36 and an inner surface 38. In the example shown, the sidewall 34 is cylindrical however other cross-sections are contemplated. The sidewall 34 can generally extend along the longitudinal axis 30. The sidewall 34 defines a plurality of inlet ports 40a, 40b, 40c, and 40d. A corresponding plurality of boss structures 42a, 42b, 42c, and 42d can extend from the outer surface 36 on the sidewall 34. Each boss structure 42a, 42b, 42c, and 42d can incorporate threads 44a, 44b, 44c, and 44d, respectively. The inlet port 40a, boss 42a, and threads 44a can collectively comprise a first threaded inlet port 48a. Similarly, the inlet port 40b, boss 42b, and threads 44b can collectively define a second threaded inlet port 48b. The inlet port 40c, boss 42c, and threads 44c can collectively comprise a third threaded inlet port 48c. The inlet port 40d, boss 42d, and threads 44d can collectively comprise a fourth threaded inlet port 48d. It will be appreciated that while the particular tubular member 12 shown in the examples herein incorporates four threaded inlet ports, additional or fewer threaded inlet ports may be incorporated thereon. Moreover, some or all of the threaded inlet ports 48a, 48b, 48c, and 48d may be provided without threads. In this regard, other coupling structures may be formed or included onto the respective bosses 42a, 42b, 42c, and/or 42d that are configured to selectively couple with a flowable material delivery device as will become appreciated herein. A series of threaded caps 49a, 49b, 49c, and 49d can threadably mate with the first, second, third and fourth threaded inlet ports 48a, 48b, 48c, and 48d, respectively. It will be appreciated that the terms "first", "second", "third" and "fourth" are used arbitrarily herein and are not meant to denote a particular priority or sequence of use.

Figure 3:
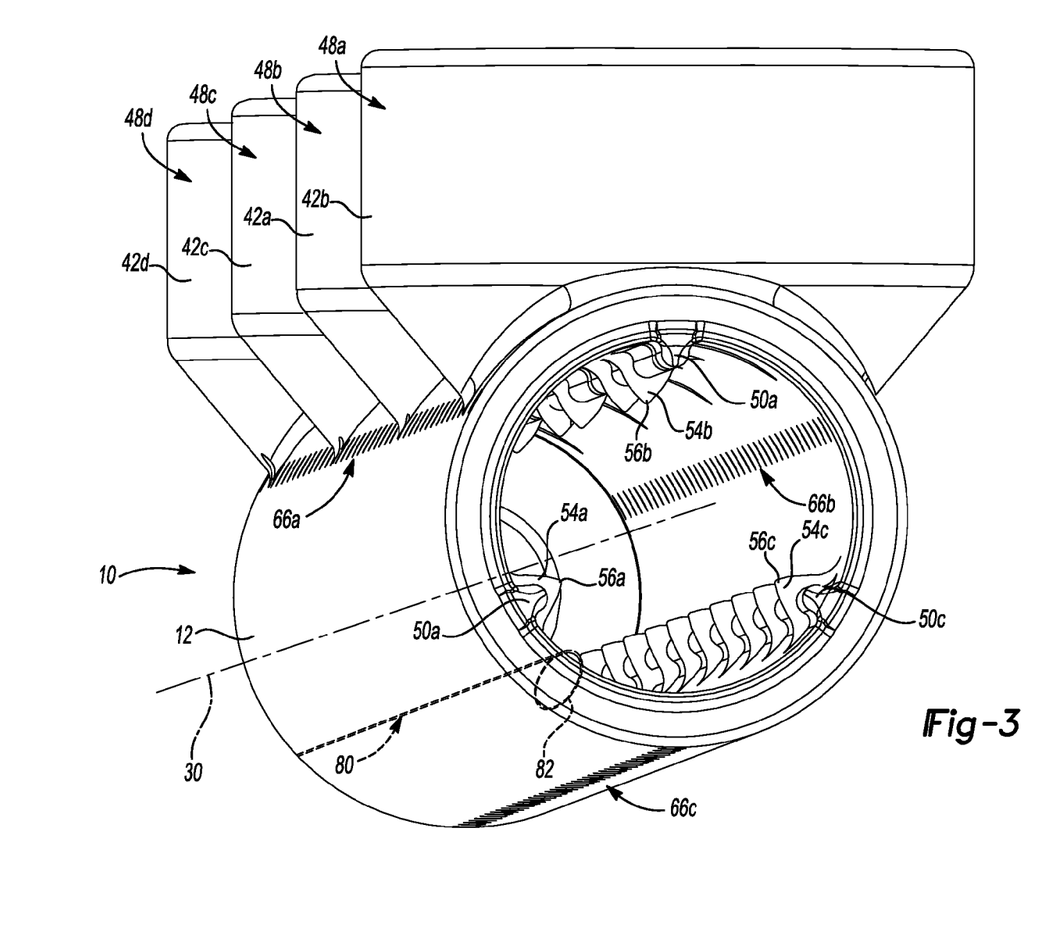
FIG. 3 is an end perspective view of the mold of FIG. 1.
Figure 6:
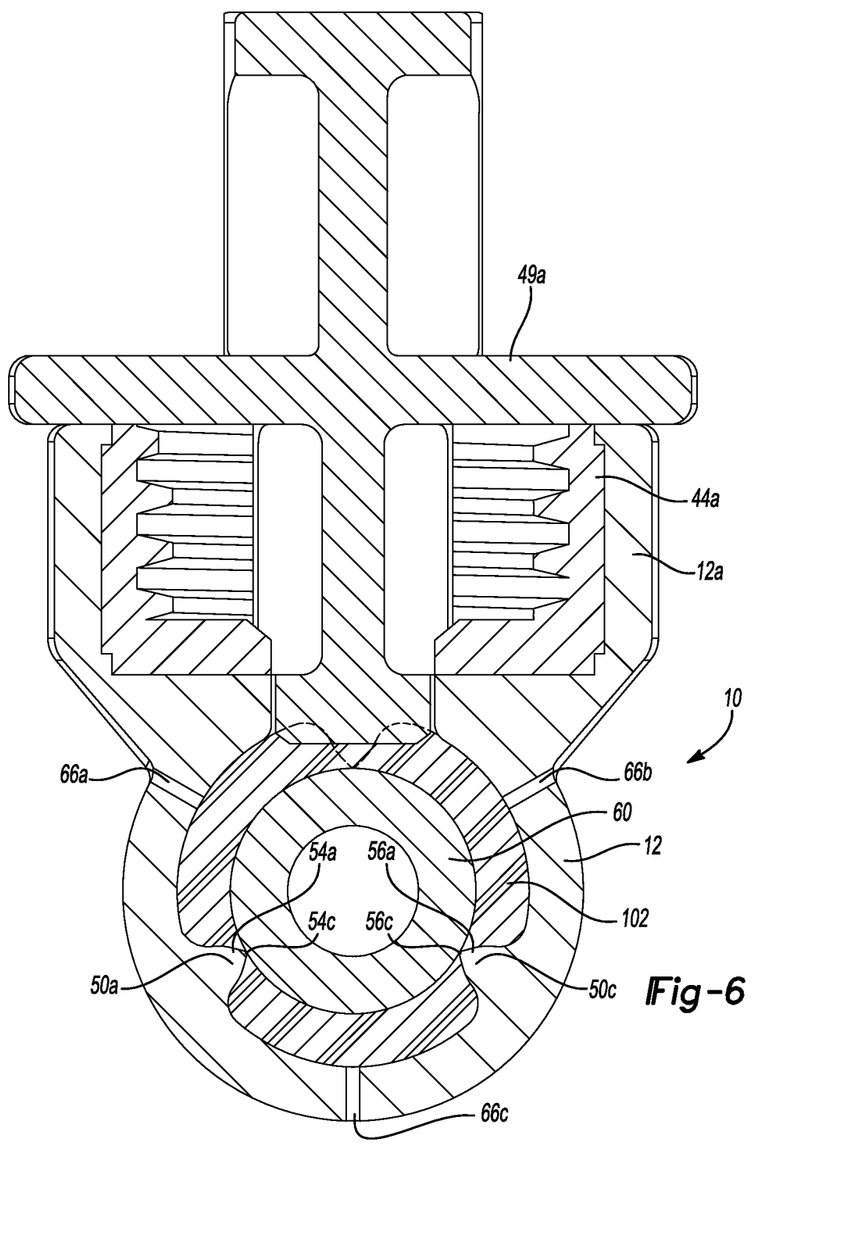
FIG. 6 is a cross-sectional view taken along lines 6-6 of FIG. 5 taken through a set of nibs extending from protrusions on an inner surface of the tubular member.
Figure 7:
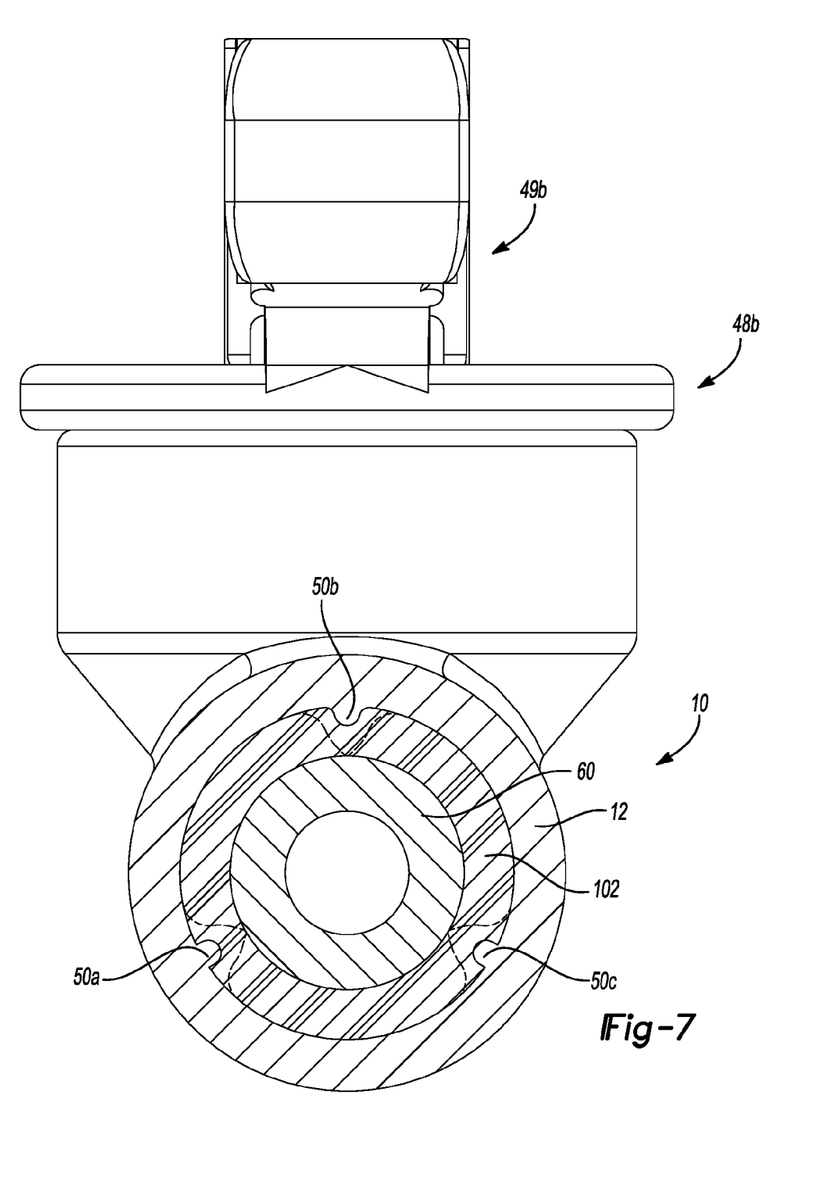
FIG. 7 is a cross-sectional view taken along lines 7-7 of the tubular member taken along a section of the tubular member without nibs.

With particular reference now to FIGS. 2 and 3, additional features of the tubular member 12 will be described. A first, second, and third protrusion 50a, 50b, and 50c, respectively, can be formed on the inner surface 38 of the sidewall 34. In the example shown, the protrusions 50a, 50b, and 50c can be radially disposed around the inner surface 38 at radially equidistant intervals. In the example shown, the protrusions 50a, 50b, and 50c are arranged at substantially 120 degrees relative to each other. Each protrusion can extend substantially along a length of the tubular member 12 between the insertion end 14 (FIG. 1) and the opposite end 16 (FIG. 1). While three protrusions are shown, it is appreciated that additional or fewer protrusions may be incorporated. According to one example, the protrusions 50a, 50b, and 50c can each include longitudinally spaced nibs 54a, 54b, and 54c extending inwardly toward the longitudinal axis 30. Each nib 54a, 54b, and 54c can have a nail engaging surface 56a, 56b, and 56c, respectively. The respective nail engaging surfaces 56a, 56b, and 56c can be configured to engage a nail 60 (FIG. 6) and offset the nail 60 inwardly along the longitudinal axis 30 and spaced from a remainder of the protrusions 50a, 50b, and 50c. As will be described, the protrusions 50a, 50b, and 50c can facilitate formation of one or more vent grooves 62 (FIG. 9) in the cement surface of a resulting cement-coated IM nail 60'. The vent grooves 62 can inhibit pressure build-up during implantation of the cement coated IM nail 60'.

With specific reference now to FIG. 3, additional features of the tubular member 12 will be described. A first, second, and third plurality of vent holes or ports 66a, 66b, and 66c can be formed through the sidewall 34. In the example shown, each row of vent ports 66a, 66b, and 66c is located generally between an adjacent pair of protrusions 50a, 50b, and 50c. The vent ports 66a, 66b, and 66c can be configured to permit air to escape the tubular member 12 during advancement of the flowable material within the tubular member 12 as will become appreciated from the following discussion.

The tubular member 12 can be formed of easily cuttable, transparent or translucent material such as silicone. The material can further be flexible and conducive to cement-releasing. In some examples, the silicone can have a reinforcing structure such as a wire mesh. The tubular member 12 can be formed in any dimensions to accommodate receipt of an IM nail (or other prosthetic implant) having any given dimension. Furthermore, and as identified above, the tubular member 12 can be cut to length to accommodate an IM nail having any length.

According to another example of the present disclosure, a pull member 80 (FIG. 3) can be incorporated into or adjacent the sidewall 34. The pull member 80 can extend partially or completely along the length of the sidewall 34 of the tubular member 12. The pull member 80 can be configured to facilitate removal of the tubular member 12 subsequent to curing of the flowable material against the IM nail. In this regard, the pull member 80 can include a pull structure 82 such as a loop or other easily graspable configuration where a user can pull the pull structure 82 generally away from the longitudinal axis 30 creating a cut or slit along and through the length of the sidewall 34 of the tubular member 12. Once the slit has been formed along the tubular member 12, the user can easily peel away the tubular member 12 to reveal the coated IM nail 60'.

With particular reference now to FIGS. 4-7, a method of coating the IM nail 60 according to one example of the present disclosure will be described. According to the present disclosure, multiple molds 10 will be provided having various inner and outer diameters. A user can select an appropriate mold 10 that suits a particular nail 60 for a given application. It will be understood that the overall length of the mold 10 can be modified such as by cutting a length off of the insertion end 14.

Figure 4:
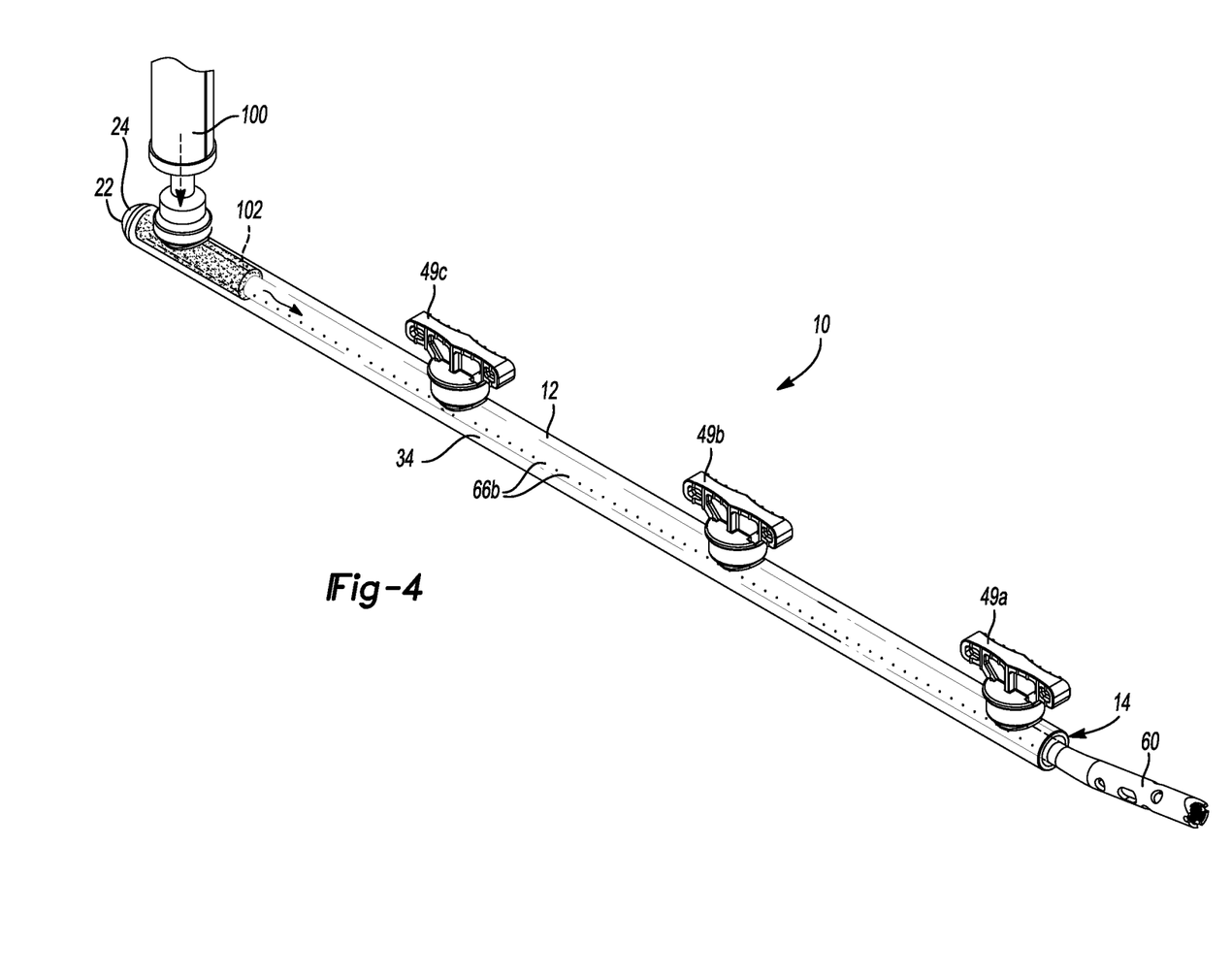
FIG. 4 is a side perspective view of the mold of FIG. 1 and shown with an IM nail inserted into the tubular member and a flowable material delivery device threadably coupled to a first port according to one example of the present disclosure.
Figure 5:
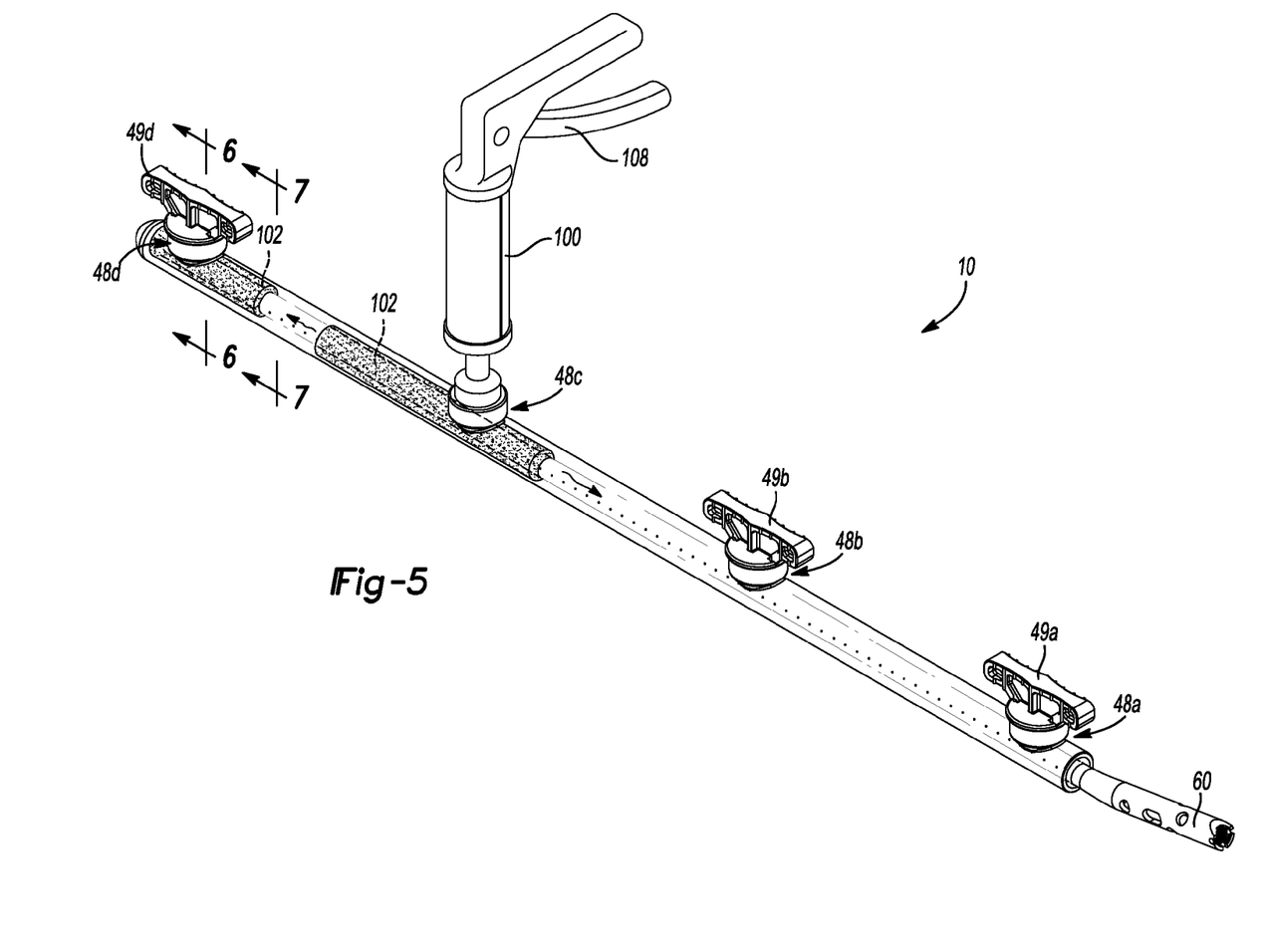
FIG. 5 is a side perspective view of the mold of FIG. 4 and shown with the flowable material delivery device moved to an adjacent threaded port subsequent to delivery of a sufficient amount of flowable material into the first port.

At the outset, the IM nail 60 can be introduced into the tubular member 12 as shown in FIG. 4. Next, one of the threaded caps, such as 49d, can be removed from its threaded inlet port, such as the threaded inlet port 48d. A flowable material delivery device 100 can be coupled to the threaded inlet port 48d. Next, a user can advance flowable material 102 through the inlet port 40d and into the tubular member 12. In the example shown, the flowable material delivery device 100 can include a handle 108 (FIG. 5) that can be actuated to influence emission of the flowable material 102 out of the delivery device 100 and into the inlet port 40d. Other configurations of the flowable material delivery device may be used. Furthermore, it will be appreciated that other connections may be made between the flowable material delivery device 100 and the respective inlet ports. For example, a luer lock coupling, a nozzle coupling or other coupling may be employed.

A user can continue to introduce the flowable material 102 into the tubular member 12 until the flowable material 102 has advanced sufficiently along a portion of the tubular member 12 toward an adjacent inlet port 40c. As the tubular member 12 is formed of a transparent material, a user can observe the flowable material 102 advancing along a length of the tubular member 12 (between the inner surface 38 of the sidewall 34 and the IM nail 60). In one example, a user can stop introduction of the flowable material 102 into the tubular member 12 once the flowable material 102 has advanced substantially, such as about three-fourths of the way, toward the adjacent inlet port 40c. Other examples are contemplated.

Next, a user can remove the flowable material delivery device 100 from the threaded inlet port 48d and replace the cap 49d onto the threaded inlet port 48d. The cap 49c can then be removed from the adjacent threaded inlet port 48c. The flowable material delivery device 100 can then be coupled to the threaded inlet port 48c. Next, a user can urge the flowable material 102 through the inlet port 40c and into the tubular member 12. Notably, the flowable material 102 can backfill toward the fourth threaded inlet port 48d as well as advance in an opposite direction toward the second threaded inlet port 48b. As can be appreciated, as the flowable material 102 backfills toward the fourth threaded inlet port 48d, the flowable material will spread evenly along the IM nail 60 between the fourth and third threaded inlet ports 48d and 48c.

The process is repeated for subsequent inlet ports along the length of the tubular member 12 until the flowable material 102 has been sufficiently coated along the length of the IM nail 60. It will be appreciated that while not necessary, in some examples, the flowable material 102 may extend out of some or all of the vent ports 66a, 66b, and 66c. Furthermore, during introduction of the flowable material 102 into the tubular member 12, the vent ports 66a, 66b, and 66c allow air to escape the tubular member 12 to accommodate introduction of the flowable material between the tubular member 12 and the IM nail 60.

Figure 8:
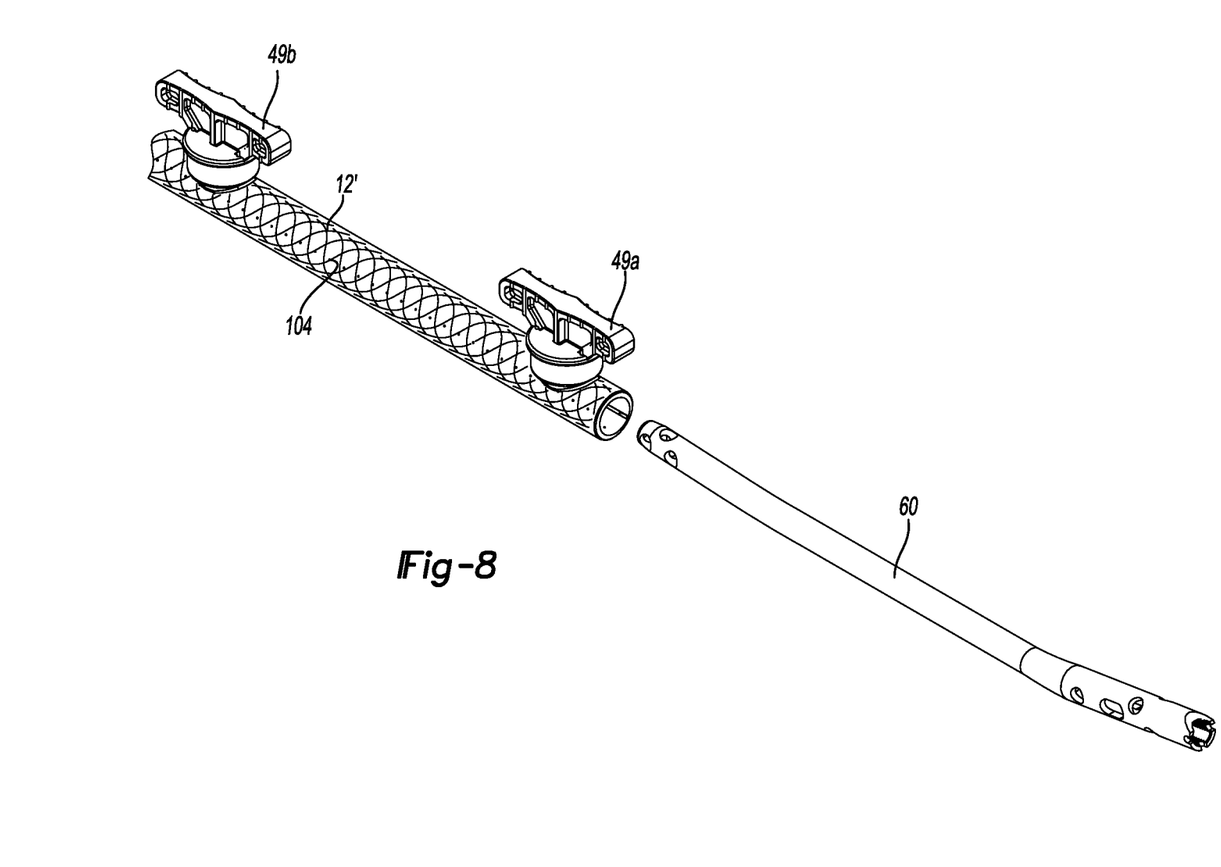
FIG. 8 is a side perspective view of a mold constructed in accordance to additional features of the present disclosure and formed of wire-reinforced silicone.

With reference to FIG. 8, a tubular member 12' constructed in accordance to additional features is shown. The tubular member 12' can include a reinforced silicone material. The reinforced silicone material can include a wire mesh 104. Other reinforcing structures may be incorporated.

Figure 9:
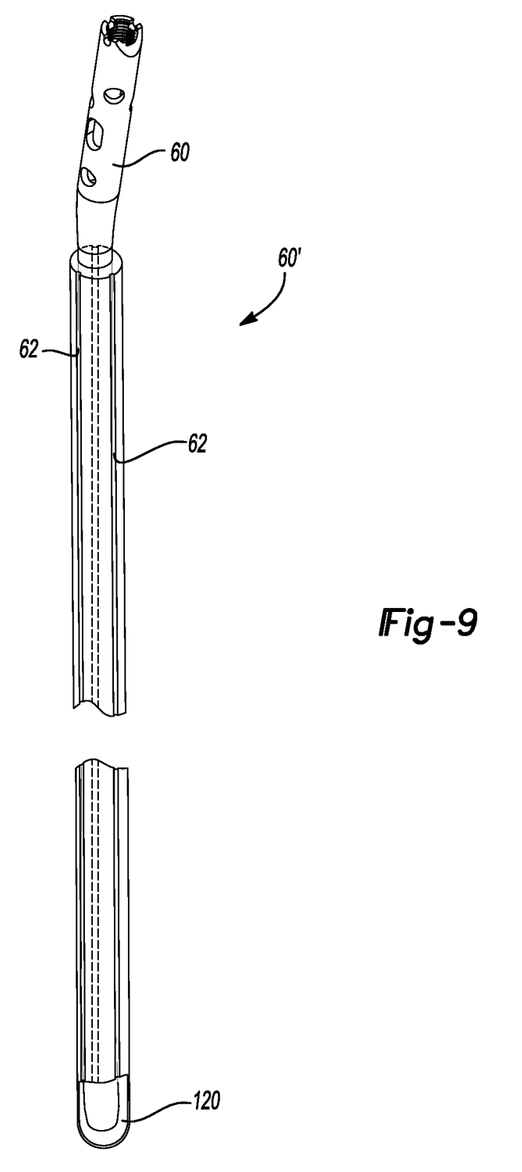
FIG. 9 is a side perspective view of a coated IM nail subsequent to removal of the mold according to one example of the present disclosure and shown having a protective membrane cover disposed around a distal end thereof to inhibit flowable material from entering the IM nail.

With particular reference to FIG. 9, once the flowable material 102 has cured a sufficient amount, the tubular member 12 can be cut away from the coated IM nail 60' and discarded. The resulting coated IM nail 60' can include the longitudinally extending grooves 62 formed therealong that can accommodate air escape and inhibit pressure build-up during implantation into an IM canal. According to a further example of the disclosure, a thin membrane sheath 120 can be incorporated onto an end of the IM nail 60 prior to insertion of the IM nail 60 into the tubular member 12. The sheath 120 can inhibit introduction of flowable material into the IM nail 60 such as through an exposed cannulation thereon. Additionally or alternatively, a plug or collection of plugs, such as formed by flexible silicone, can be inserted into screw holes or the cannulation of the nail to inhibit introduction of flowable material into the IM nail 60.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Non-limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on", "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

What is claimed is:

1. A method of coating an intramedullary (IM) nail with flowable material, the method comprising:
    advancing the IM nail into a tubular member from an insertion end of the tubular member toward an opposite end of the tubular member, wherein advancing the IM nail includes slidably translating the IM nail along at least two longitudinally extending protrusions formed on an inner cylindrical surface of a sidewall of the tubular member;
    advancing flowable material through a first port defined through the sidewall at a first location on the tubular member;
    subsequent to curing of the flowable material, removing the tubular member from the IM nail having the cured flowable material thereon.

2. The method of claim 1 wherein advancing the IM nail comprises advancing the IM nail into the tubular member until a distal end of the IM nail engages a concave surface at the opposite end of the tubular member.

3. The method of claim 1 further comprising:
    coupling a flowable material delivery device to a boss formed on the tubular member proximate to the first port.

4. The method of claim 3 wherein coupling comprises one of threadably coupling, luerjoe lock coupling, and nozzle coupling the flowable material delivery device to the tubular member.

5. The method of claim 1 further comprising:
advancing flowable material through a second port defined through the sidewall at a second location, distinct from the first location, on the tubular member.

6. The method of claim 5, further comprising:
observing the flowable material advancing within the tubular member; and
stopping the advancing of the flowable material through the first port based on the flowable material advancing substantially toward the second port.

7. The method of claim 1 wherein removing the tubular member comprises cutting the tubular member away from the coated IM nail.

8. The method of claim 1 wherein removing the tubular member comprises pulling a pull member disposed on the tubular member causing a slit to be formed along the tubular member.

9. The method of claim 1, further comprising disposing a sheath onto an end of the IM nail prior to the advancing of the IM nail into the tubular member.

10. A method of coating an intramedullary (IM) nail with flowable material, the method comprising:
advancing the IM nail into a tubular member from an insertion end of the tubular member toward an opposite end of the tubular member until a distal end of the IM nail engages a concave surface at the opposite end of the tubular member;
advancing flowable material through a first port defined through a sidewall at a first location on the tubular member;
subsequent to curing of the flowable material, removing the tubular member from the IM nail having the cured flowable material thereon.

11. The method of claim 10, further comprising disposing a sheath onto an end of the IM nail prior to the advancing of the IM nail into the tubular member.

12. A method of coating an intramedullary (IM) nail with flowable material, the method comprising:
disposing a sheath onto an end of the IM nail;
advancing the IM nail into a tubular member from an insertion end of the tubular member toward an opposite end of the tubular member;
advancing flowable material through a first port defined through a sidewall at a first location on the tubular member;
subsequent to curing of the flowable material, removing the tubular member from the IM nail having the cured flowable material thereon.

* * * * *